United States Patent [19]
Gubernick et al.

[11] Patent Number: 6,036,965
[45] Date of Patent: Mar. 14, 2000

[54] TOURMALINE IN COSMETIC CLEANSING COMPOSITIONS

[75] Inventors: Joseph Gubernick, New York; Gheorghe Cioca, Lake Grove; Andrew J. Bevacqua, E. Setauket; Charles Craig Tadlock, Islip Terrace, all of N.Y.

[73] Assignee: Color Access, Inc., Melville, N.Y.

[21] Appl. No.: 09/039,013

[22] Filed: Mar. 13, 1998

[51] Int. Cl.⁷ ....................................................... A61K 6/00
[52] U.S. Cl. .................. 424/401; 424/70.19; 424/70.28; 424/70.11; 510/130; 510/139; 510/150; 514/846
[58] Field of Search ................................ 424/401, 70.19, 424/70.28, 70.11; 514/846; 510/122, 130, 139, 140, 150

[56] References Cited

U.S. PATENT DOCUMENTS

| | | |
|---|---|---|
| 4,857,306 | 8/1989 | Roller . |
| 5,309,739 | 5/1994 | Lee . |
| 5,599,455 | 2/1997 | Hukai . |
| 5,683,683 | 11/1997 | Scafidi ................... 424/70.19 |
| 5,710,114 | 1/1998 | Pyles ....................... 510/123 |

FOREIGN PATENT DOCUMENTS

| | | |
|---|---|---|
| 6173162 | 6/1994 | Japan . |
| 7024444 | 1/1995 | Japan . |
| 8057060 | 3/1996 | Japan . |
| 9-194321 | 7/1997 | Japan . |
| 9-278624 | 10/1997 | Japan . |
| 9-278632 | 10/1997 | Japan . |
| 10-94963 | 7/1998 | Japan . |
| 10-248904 | 9/1998 | Japan . |
| 10-262856 | 10/1998 | Japan . |
| 10-305073 | 11/1998 | Japan . |
| 11-004713 | 1/1999 | Japan . |
| 11-032937 | 2/1999 | Japan . |
| 11-057038 | 3/1999 | Japan . |

OTHER PUBLICATIONS

Hydroxyl ions and surface active actions of tourmaline used in cosmetics. Adam Kozan Chuo Kenkyusho Co., Ltd. Ohmiya–shi saitama–ken, Japan, May 1997.

Analysis Data of Tourmaline Mineral, Yutaka Sangyou, Inc., K. Shinohara and Central Research Institute of Adan Mine Inc., J. Okamoto (estimated date 1995).

Hydroxyl Ions and Surface Active Actions of Tourmaline Used in Cosmetics, Adam Kozan Chuo Kenkyusho Co., Ltd., Ohmiya–shi Saitama–ken, Japan.

Lovion's UCHU Hair and Scalp Treatments, published 1998.

BodySpark Far Infrared and Negative Ion Products, published 1999, VORTEX U.S.A.

*Primary Examiner*—Thurman K. Page
*Assistant Examiner*—Lakshmi Channavajjala
*Attorney, Agent, or Firm*—Kenyon & Kenyon

[57] ABSTRACT

The present invention relates to cosmetic skin or hair cleansing compositions comprising tourmaline.

12 Claims, No Drawings

TOURMALINE IN COSMETIC CLEANSING COMPOSITIONS

FIELD OF THE INVENTION

The invention relates to cosmetic compositions. More particularly, the invention relates to cosmetic compositions for skin or hair cleansing.

BACKGROUND OF THE INVENTION

Tourmaline is a complex borosilicate mineral with a variety of unusual pyroelectric and piezoelectric properties. It is probably best known for its use as a gem stone; however, in recent years, it has begun to find a number of other uses that are in one way or another connected to its unique electrical activity, which results from the presence of permanent electrodes within the crystalline structure. In particular, tourmaline in water produces an electrical discharge which dissociates the water molecule into hydrogen and hydroxyl ions, which in turn produce hydronium ions ($H_3O^+$) and hydrated hydroxyl ion ($H_3O_2^-$) by their reactions with $H_2O$ molecules. Both these ions are reported to have surface active properties.

These observations have resulted in the use of tourmaline in a variety of different industrial products and methods. For example, U.S. Pat. No. 5,599,455 discloses a system for water treatment in which tourmaline is used in an ion generator to generate hydronium and hydroxyl ions in the water, with the reported result of "high surface activity" in the water, which is then recommended for use in detergent free washing in washing machines and in cleaning oil-contaminated machinery. In a similar vein, U.S. Pat. No. 5,309,739 discloses a tourmaline coating applied to a surface of a washing machine with the intent of forming hydroxyl ions in the wash water to aid in cleansing. It has also been disclosed (JP 7024444) as being used in powder form in a shower apparatus to treat chlorinated water, so as to alter the chlorine structure, allowing it to retain its water-purifying activity, while reducing the possible negative effects of chlorine.

Tourmaline has also, in connection with its electrical properties, been suggested as being useful in promoting physical well-being. For example, JP 6173162 discloses fabric coated with a film containing tourmaline, which fabric is made into clothing which is said to provide an electrical stimulus to the wearer's skin, to improve the wearer's health. Likewise, JP 8057060 discloses a "health therapeutic tool" based on a substrate incorporating powdered tourmaline and a diode, which tool is applied to the skin to achieve a therapeutic effect.

The use of tourmaline in cosmetics has also been proposed. JP 9194321 suggests the use of very fine tourmaline powder as an antiseptic in cosmetic products. In addition, U.S. Pat. No. 4,857,306 suggests the use of pure powder of semi-precious stones, including tourmaline, as a decorative addition to cosmetic compositions. However, tourmaline has not previously been used in cleansing cosmetic compositions.

SUMMARY OF THE INVENTION

The present invention relates to cleansing compositions for the skin or hair comprising an effective amount of tourmaline. The invention also relates to a method for cleansing the skin or hair which comprises applying to the skin or hair an effective amount of tourmaline. The compositions have excellent cleansing ability, and yet are gentle and non-irritating on the skin of the user.

DETAILED DESCRIPTION OF THE INVENTION

The compositions of the invention comprise a cleansing effective amount of tourmaline. Generally, the effective amount of tourmaline use is in the range of from about 0.01–99.5%, more commonly between 0.01–20%, by weight of the total composition, the amount depending upon the nature of the composition. There are a variety of forms of tourmaline. The mineral is usually found in crystal form, with a structure based on a six-sided silicate ring($Si_6O_{18}$) and $BO_3$ groups, with a generic formula:

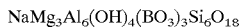

$$NaMg_3Al_6(OH)_4(BO_3)_3Si_6O_{18}$$

However, substitutions within the formula can occur, in that calcium may replace part of the sodium; lithium, aluminum or ferrous iron can replace part of the magnesium; ferric iron can replace the aluminum; and fluorine can replace the hydroxyl group. Potassium, chromium and manganese can also be found in tourmaline. To the extent these forms are cosmetically acceptable, any form can be used in the compositions of the invention. By cosmetically acceptable is meant any form of tourmaline which will not cause harm to humans or other recipient organisms.

The tourmaline used in the invention can be in any form convenient to the intended use of the final product. Generally, for a cleanser, it will be preferred that the tourmaline be ground to a relatively small particle size, for example from about 0.1 $\mu$ to about 10 mm. In particular, particle sizes at the smaller end of this range, for example, between 1–10 $\mu$, can be used for reasons of aesthetics, and ease of combination with the remaining components of the composition; however, larger particle sizes may be appropriate when a physical exfoliation action is also desired, for example in a body cleansing product. Tourmaline in its various forms is available from a wide range of commercial sources; useful tourmaline powders, for example, are produced by Adam Kozan Chuo Kenkyusho Co., Ltd., Saitama, Japan.

The tourmaline can be incorporated into a variety of cosmetic cleansing products. For example, tourmaline can be used in facial cleansing compositions, or in hair or body shampoos or cleanser. Depending on the nature of the composition, the tourmaline will ordinarily be combined with other components which aid in cleansing and/or conditioning of the surface to which the composition is applied. In a facial cleanser, for example, additional components can include one or more of the milder surfactants; examples include, but are not limited to the amphoteric surfactants, such as alkvl betaines, amido alkyl betaines, sulfobetaines, and N-alkyl-amino propionates; or mild anionics, such as fatty acid carboxylates, taurates, sulfosuccinates, isethionates, taurates, and sarcosinates, or monoalkyl phosphates. Other desirable components of facial cleansers can include skin conditioning agents, such as humectants or emollients; viscosity modifiers, such as gums, cellulose derivatives, PEG esters and carbopol resins; and biologically active materials, such as hydroxy acids, antiinflammatories, or anti-irritants. In the latter case, the surface active properties of the tourmaline may enhance delivery of the active agents.

The cleansing composition can also be a hair or body shampoo or cleanser. Like the facial cleanser, hair or body shampoos will contain surfactants or detergents for cleansing, for example, anionic sulfates, such as alkyl sulfates and alkyl ether sulfates, mono- and disulfosuccinates, alpha-olefin sulfates, and monoglyceride sulfates, as well as those surfactants useful for facial cleansing. Shampoos also will usually contain foam boosters, which are usually non-ionic surfactants, such as alkanolamides or N-alkylpyrrolidones; and conditioning agents, such as amine oxides, silicone surfactants such as amodimethicone or dimethicone copolyol, and cationic polyquaternium surfactants. Also frequently added to hair shampoos are active components such as antidandruff agents, e.g., zinc pyrithione or pyroctone olamlne. The process for formulation of cleansing products is well known in the art, and additional possible components for such formulations can be found, for example, in The International Cosmetic Ingredient Handbook, Third Edition, 1996, the contents of which are incorporated herein by reference.

The tourmaline can also be used as the cleansing element in a solid substrate used for cleaning the skin or hair. For example, the tourmaline can be impregnated onto or into paper or cloth, for use as a washcloth, disposable wipes, napkins, and the like. Alternately, the tourmaline can be incorporated into a sponge, loofah, or similar applicator. In some of these cases, as is apparent, water will be added to the substrate at the time of use. As used in the present specification and claims, "cleansing composition" shall also encompass such devices in which tourmaline forms the cleansing element.

In all cases, the cleansing products benefit from the presence of tourmaline in that it permits a reduction in the amount of detergent-type surfactant that needs to be used to achieve proper cleansing; the latter are often perceived by the consumer to be irritating, and therefore, any reduction in the amount used is beneficial. The products containing tourmaline, because of a reduction in surfactants, are thus relatively mild and gentle to the skin. Tourmaline is also effective in the process of oil removal from substrates, and therefore, is particularly suitable for use in cleansers intended for use on oily skin or hair.

The invention is further illustrated by the following non-limiting examples.

EXAMPLES

Example I

A facial cleansing composition according to the invention is prepared as follows:

| Material | Weight % |
| --- | --- |
| Cocamidopropyl hydroxysultaine | 14.00 |
| Coco/oleamidopropyl betaine | 16.00 |
| TEA-Cocoyl glutamate | 15.00 |
| Sodium cocoyl sarcosinate | 19.00 |
| Sodium laureth sulfate | 9.00 |
| Polyquaternium-6 | 0.40 |
| Methyl paraben | 0.40 |
| propyl paraben | 0.40 |
| water | QS |
| Tourmaline* | 0.05 |

*Red tourmaline, particle size about 1.7$\mu$, from Adam Kozan

The components are blended together by conventional mixing techniques.

The presence of a small amount of tourmaline in this formula permits the reduction of surfactants in the formula by almost 20%, relative to a substantially identical formula containing no tourmaline, with no loss of cleansing ability.

What we claim is:

1. A method of cleansing the skin or hair which comprises applying to the skin or hair a composition comprising an effective amount of tourmaline in combination with a cosmetically acceptable carrier.

2. The method of claim 1 in which the amount of tourmaline comprises from about 0.01–99.5% by weight.

3. The method of claim 1 which comprises from about 0.01–20% of tourmaline by weight.

4. The method of claim 1 in which the composition comprises a tourmaline powder having a particle size of about 0.1$\mu$–10 mm.

5. The method of claim 1 in which the composition comprises a tourmaline powder having a particle size of about 1–10$\mu$.

6. The method of claim 1 in which the composition further comprises at least one surfactant.

7. The method of claim 1 in which the composition further comprises a conditioning agent.

8. The method of claim 1 in which the composition further comprises a foam booster.

9. The method of claim 1 in which the composition is a facial cleaner.

10. The method of claim 1 in which is the composition is a hair or body shampoo.

11. The method of claim 1 in which the tourmaline is incorporated into or onto a solid substrate.

12. The method of claim 1 in which the substrate is a paper, cloth, sponge, or loofah.

* * * * *